United States Patent [19]
Stauffer

[11] Patent Number: 6,137,017
[45] Date of Patent: Oct. 24, 2000

[54] METHANOL PROCESS FOR NATURAL GAS CONVERSION

[76] Inventor: John E. Stauffer, 6 Pecksland Rd., Greenwich, Conn. 06831

[21] Appl. No.: 09/361,949

[22] Filed: Jul. 27, 1999

Related U.S. Application Data

[63] Continuation-in-part of application No. 08/970,056, Nov. 13, 1997, abandoned, which is a continuation-in-part of application No. 08/533,124, Sep. 25, 1995, abandoned.

[51] Int. Cl.⁷ ..................................................... C07L 27/00
[52] U.S. Cl. .............................................. 568/893
[58] Field of Search .............................................. 568/893

[56] References Cited

U.S. PATENT DOCUMENTS

| | | |
|---|---|---|
| 4,990,696 | 2/1991 | Stauffer . |
| 5,185,479 | 2/1993 | Stauffer . |

OTHER PUBLICATIONS

Kramers, "Elements of Chemical Reactor Design and Operations," pp. 38–39, 1973.
H. Kramers and K.R. Westerterp, Elements of Chemical Reactor Design and Operation, book, 1973, 38–39, Academic Press, Inc., New York.

*Primary Examiner*—Michael L. Shippen
*Attorney, Agent, or Firm*—Young & Basile

[57] ABSTRACT

A process is provided for producing methyl alcohol from natural gas using chlorination technology. The process includes reacting methyl chloride, hydrogen chloride, oxygen and perchloroethylene in a catalytic reactor to give methanol product and hexachloroethane and using the $C_2Cl_6$ to chlorinate methane of natural gas feedstock in multiple thermal chlorination reactors, each with a natural gas recycle loop. These reactors are arranged in a cross-flow reactor system whereby a gas purge from the first reactor is fed to the second, and so on if necessary until a last reactor, which is vented to the atmosphere by feeding a purge steam to the catalytic reactor.

5 Claims, 1 Drawing Sheet

METHANOL PROCESS

METHANOL PROCESS FOR NATURAL GAS CONVERSION

This is a continuation-in-part of U.S. Ser. No. 08/970,056 filed Nov. 13, 1997 now abandoned, which is a continuation-in-part of U.S. Ser. No. 08/533,124 filed Sep. 25, 1995 now abandoned.

FIELD OF THE INVENTION

The present invention relates to an improvement in processes designed to produce methyl alcohol from natural gas using chlorination technology. The improvement permits the use of natural gas containing significant levels of inert gases while achieving high methane efficiencies. The process encompasses the use of multiple thermal chlorination reactors, each with a natural gas recycle loop. These reactors are arranged in a cross-flow reactor system whereby the gas purge from the first thermal reactor is fed to the second, and so on until the last thermal reactor, which is vented to the atmosphere.

BACKGROUND OF THE INVENTION

Processes for the manufacture of methyl alcohol from methane are described in U.S. Pat. No. 4,990,696 and U.S. Pat. No. 5,185,479, which are incorporated in their entirety by reference in this specification. In both of these references, methane was assumed to be the raw material. Thus, no provisions were made for a purge to remove inert gases that are invariably found in natural gas.

In practice, pure methane would be impractical to use for methyl alcohol production on a large scale. Its high cost and lack of availability would preclude such an application. Instead, the source of methane would generally be natural gas. Although inexpensive and abundant, natural gas presents difficulties in its use caused by the fact that it contains a number of constituents besides methane. For example, natural gas from one source was reported to contain 96 percent methane by volume, 3.2 percent nitrogen and 0.8 percent carbon dioxide. Another source contained 80.5 percent methane, 18.2 percent ethane and 1.3 percent nitrogen. Commonly, natural gas may contain anywhere from 0.1 percent to over 7 percent inerts.

Although hydrocarbons other than methane can quite easily be extracted from natural gas, inerts present a more difficult challenge. Such inerts include nitrogen and carbon dioxide. In contrast to conventional processes for producing methanol via synthesis gas, technology based on chlorination chemistry cannot handle carbon dioxide. This gas, therefore, must be treated in the same manner as other inerts, notably nitrogen.

The problem of using natural gas as a raw material for methanol production is compounded by the side reactions encountered in chlorination chemistry. In the chlorination of methane to methyl chloride, the latter compound is further chlorinated to give decreasing quantities of methylene chloride, chloroform and carbon tetrachloride. In order to maximize the yields of methyl chloride, it is necessary to use an excess of methane. This condition can be realized by recycling unreacted methane to the reactor. This procedure, however, leads to the build up of unacceptable levels of inerts in the recycle stream when natural gas is the feed.

Further complicating the recycle of methane is the need to separate hydrogen chloride gas from the recycle stream. Several methods are available for separating hydrogen chloride from methane, but each one has drawbacks. The aforementioned references disclose the use of stripper-absorber columns employing hydrochloric acid solutions to remove hydrogen chloride. The utility requirements for these units, however, are considerable. Alternative means for separating hydrogen chloride from methane include the use of gas separation membranes or adsorbents. But neither of these approaches are entirely satisfactory since they require either elevated pressures or temperatures for their operation.

It is therefore an object of the present invention to provide a process which overcomes the disadvantages of existing technology for producing methyl alcohol.

A further object is to be able to handle a wide variety of natural gas feedstocks while achieving high yields of product in an environmentally friendly process.

Still another object is to provide for a practical process by reducing investment and operating costs to a minimum.

These and other objects, features and advantages of the invention will be apparent from the following description and the accompanying drawing.

SUMMARY OF THE INVENTION

In one preferred embodiment of the invention, methyl chloride is hydrolyzed with water over a catalyst to give methyl alcohol and hydrogen chloride. In the same catalytic reactor, perchloroethylene is oxychlorinated with hydrogen chloride and oxygen to produce hexachloroethane and water. With the balancing of these reactions, there is no net production of water, so that the overall reaction can be stated as the reaction of methyl chloride, hydrogen chloride, perchloroethylene and oxygen to give hexachloroethane and methyl alcohol.

Methyl chloride, which is required for the catalytic reaction, is produced by chlorinating natural gas with hexachloroethane in a thermal chlorination reactor. The methane content of the natural gas is chlorinated to methyl chloride and lesser quantities of methylene chloride, chloroform and carbon tetrachloride. Also, hydrogen chloride and perchloroethylene are produced in the chlorination reactions.

In order to suppress the formation of the higher chlorinated methane compounds, an excess of natural gas is fed to the thermal reactor. This excess natural gas leaves the reactor with the reaction products. To avoid its loss, the excess natural gas is recycled to the reactor after first separating the reaction products including hydrogen chloride, methyl chloride and perchloroethylene.

To separate these reaction products, the exit gas stream from the thermal reactor is first cooled to condense the perchloroethylene along with most of the methyl chloride as a liquid condensate. Uncondensed gases comprising methane, hydrogen chloride and inerts are sent to an absorber where the hydrogen chloride and additional methyl chloride is removed by scrubbing the gases with methyl alcohol thus providing spent methyl alcohol. The gas stream now free of hydrogen chloride, is passed to a second absorber in which methyl alcohol vapor is removed by scrubbing with the condensed perchloroethylene thus providing spent condensate solution. The scrubbed gas comprising mostly methane and inerts is recycled to the reactor. Scrubbing solutions from both absorbers are fed to the catalytic reactor.

As noted, inerts in the natural gas are not separated. Thus, the levels of these gases, including nitrogen and carbon dioxide, quickly build up in the recycle stream. In order to limit the concentration of these inerts, a purge stream must be taken from the reactor through the gas recycle loop.

Conceivably the purge stream could be vented to the atmosphere, but such a procedure would lead to significant losses of methane. The present invention provides for the recovery of this methane by feeding the purge stream to a second thermal chlorination reactor. The configuration of this second thermal reactor is very much like the first, comprising a natural gas recycle loop and a purge stream of its own. This second purge stream may be vented or fed to yet another thermal chlorination reactor.

The number of thermal chlorination reactors used will depend on such factors as the concentration of inerts in the natural gas feed, the price of the natural gas, investment costs, and operating efficiencies. The reactors will be connected in a cross-flow reactor system such that natural gas is fed to the first reactor, the purge from the first reactor is fed to the second reactor, the purge from the second reactor is fed to the third reactor (not shown), and so on until the last reactor, which is vented to the atmosphere. In order to vent the final purge stream, it is fed to the catalytic reactor to recover traces of methyl chloride and other organics. Such a procedure is designed to prevent the release of chlorinated hydrocarbons to the environment. Depending on the number of reactors installed, the quantity of unreacted methane which is ultimately vented can be reduced to any desirable level.

BRIEF DESCRIPTION OF THE DRAWINGS

The invention will be better understood by reference to the preferred embodiments illustrated in the accompanying drawing.

DETAILED DESCRIPTION OF THE PROCESS

Figure 1:
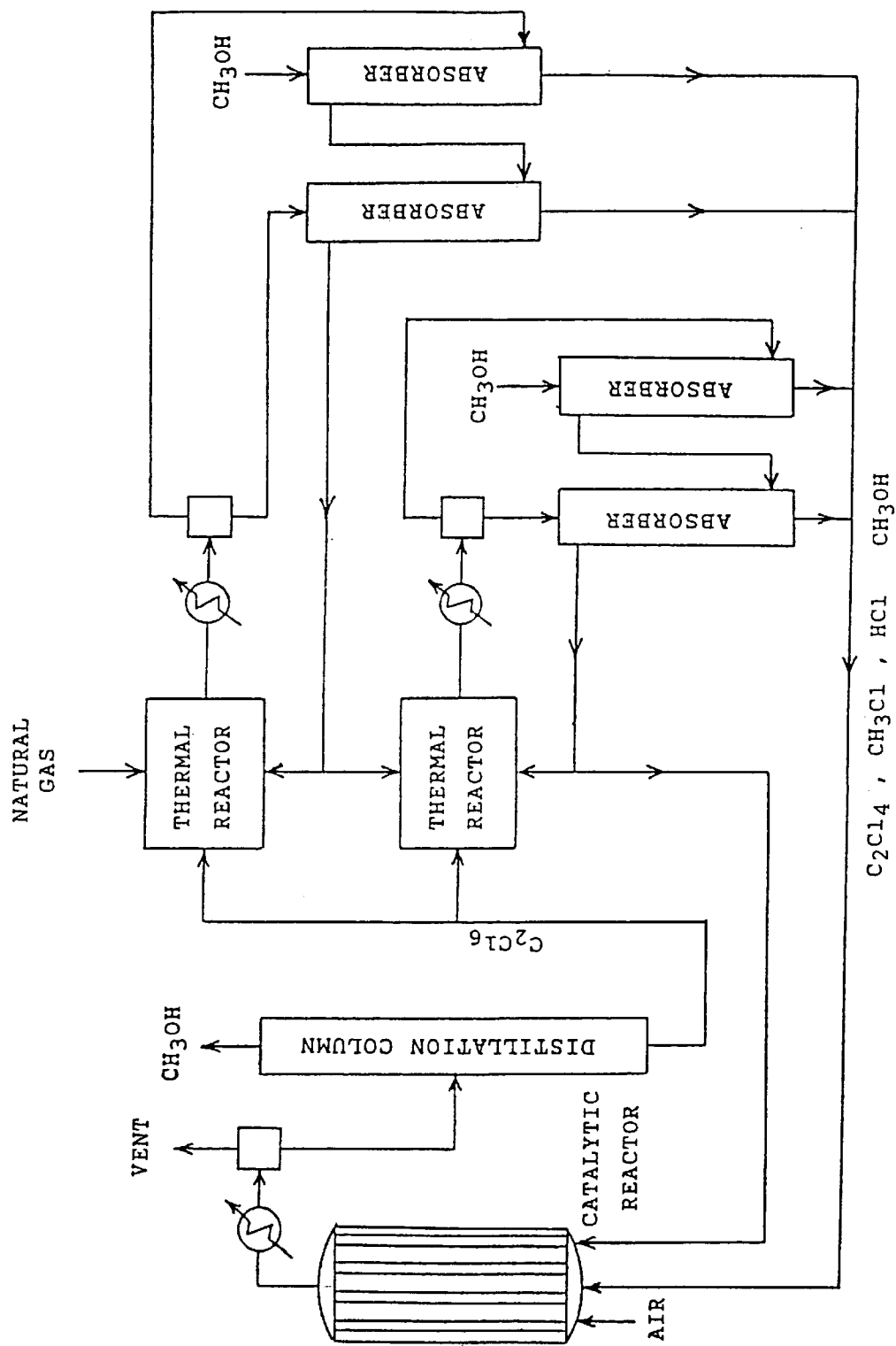
FIG. 1 is a flow sheet of the process showing the catalytic reactor, first and second thermal chlorination reactors arranged in a cross-flow reactor system, recycle loops for both thermal reactors, and lines connecting these units to provide a unified process.

The process of the present invention for the production of methyl alcohol from natural gas comprises the following steps:

reacting methyl chloride, hydrogen chloride, oxygen and perchloroethylene in a catalytic reactor to give reaction products comprising methyl alcohol and hexachloroethane, separating the methyl alcohol from the hexachloroethane, reacting the isolated hexachloroethane with natural gas in multiple thermal chlorination reactors comprising at least first and second thermal chlorination reactors, which said second thermal chlorination reactor may be the last reactor in said combination, to produce methyl chloride, hydrogen chloride, perchloroethylene and unreacted natural gas, said reactors being arranged in a cross-flow reactor system such that the natural gas is fed to the first reactor, and further such that a purge stream from said first reactor is fed to the second reactor, and so on until the last reactor, which is vented to the atmosphere by feeding a purge stream from said last reactor to the catalytic reactor, separating methyl chloride, hydrogen chloride and perchloroethylene from unreacted natural gas in the exit streams from each of the respective thermal chlorination reactors, recycling the resulting natural gas streams back to the respective reactors, and returning the separated methyl chloride, hydrogen chloride and perchloroethylene to the catalytic reactor.

The design of a continuous cross-flow reactor system has been described in the reference work, *Elements of Chemical Reactor Design and Operation* by H. Kramers and K. R. Westerterp, Academic Press Inc., New York, 1963, pages 38 and 39. Instead of supplying the total feed stream to the reactor system at one point only and withdrawing product at one outlet point as is the case with a single reactor, the cross-flow reactor system provides for a distributed feed and/or a distributed take-off along the length of the reactor system. For example, one reactant may be fed entirely to the first reactor of two or more reactors connected in a cross-flow reactor system while a second reactant is distributing to each of the reactors. Likewise product may be withdrawn from each of the separate reactors. Kramers proposes the use of cross-flow reactor systems for the purpose of suppressing undesired side reactions. By contrast, the present invention uses this design concept not to minimize the formation of byproducts but to reduce the losses of unreacted methane in the purge stream.

Both aforementioned hydrolysis and oxychlorination reactions are carried out in a catalytic reactor of shell and tube design. The catalyst, comprising optionally of salts of copper, zinc, potassium and other metals found to be efficacious, is deposited in the tubes of said reactor. A fairly wide temperature range has been reported for the reactions in question, but generally temperatures between 200° and 375° C. are preferred. The overall reaction which takes place is the reaction of methyl chloride, hydrogen chloride, oxygen and perchloroethylene to form methyl alcohol and hexachloroethane. The oxygen may be supplied by air feed to the catalytic reactor.

The effluent stream from the catalytic reactor is cooled to condense the liquids. Noncondensed gases are vented. The liquid condensate is fractionated in a distillation column to separate the methyl alcohol product from the hexachloroethane. Since hexachloroethane is a solid which sublimes at close to 186° C., it may be dissolved in an excess of perchloroethylene in order to transport it to the thermal reactors.

In the first thermal reactor, hexachloroethane is reacted with natural gas to convert methane to methyl chloride. Hydrogen chloride and perchloroethylene are also formed in this reaction. The reaction is carried out in the range of 400° to 700° C. The reactor design consists of a single tube in which a static mixer may be inserted to promote plug flow. The exit gases from the first thermal reactor are cooled to condense the liquids including a substantial fraction of the methyl chloride which is dissolved in the perchloroethylene. Uncondensed gases comprising methane, hydrogen chloride and inerts are sent to a first absorber in which methanol is used to remove the hydrogen chloride. The scrubbed methane is sent to a second absorber where the condensate from the first thermal reactor is used to remove methanol vapors from the natural gas stream. The methane stream, now free of hydrogen chloride and any methanol, is recycled back to the first thermal reactor. The liquid streams from both absorbers are fed to the catalytic reactor.

In the scrubbing of the natural gas recycle stream, it should be noted that methyl alcohol is an excellent solvent for hydrogen chloride. At 20° C. and 1 atmosphere pressure, 47.0 gms. of hydrogen chloride are absorbed in 100 gms. of saturated solution of methyl alcohol. Methyl chloride is also soluble in methyl alcohol. The condensate from the thermal reactor effluent comprises mostly perchloroethylene, which is an excellent solvent for methyl alcohol. Thus, all traces of methyl alcohol can be removed from the recycle and purge streams prior to their being fed to the thermal reactors. In this manner, anhydrous conditions can be maintained in this part of the process.

A purge stream is taken from the natural gas recycle loop in order to remove inerts. This purge stream is fed to a second thermal reactor which is very much like the first. As shown in FIG. 1 the purge from the second thermal reactor is fed to the catalytic reactor to recover traces of chlorinated hydrocarbons. The inerts are ultimately vented to the atmosphere along with the nitrogen from the air supply fed to the catalytic reactor.

The construction of the thermal reactors is quite simple and relatively inexpensive. Because thermal chlorination involves a chain reaction, it is fast, and the reactors are modest in size. The second reactor is considerably smaller than the first and if a third one is required, it would be even smaller. The considerations of size also apply to the absorbers used in the recycle loops. If, for example, the second reactor is one fifth the size of the first, then the absorbers for the second recycle loop can be scaled accordingly. Helping to reduce dimensions even further, the entire process including the catalytic reactor can be operated at elevated pressures. A range from 1 to 10 bar is recommended.

The design of the present invention is based on established principles of chemical engineering. The design avoids the use of catalysts in the chlorination of natural gas for the purpose of improving the yield of methyl chloride. It achieves the same results by controlling the concentrations of reactants and products in the reaction. By not relying exclusively on the use of catalysts, the reliability and economics of the process are enhanced.

A key feature of the process is its flexibility. A wide range of natural gas sources can be considered. Lower grades of natural gas containing higher levels of inerts can be handled efficiently. Because of its flexibility, reliability and favorable economics, the present invention can make a significant contribution to the technology of producing methyl alcohol. With the increasing worldwide demand for methyl alcohol, the utility of the present invention is assured.

EXAMPLE 1

Engineering calculations were made to determine the operating variables for an installation comprising two thermal chlorination reactors arranged in a continuous cross-flow reactor system. This is the design shown in FIG. 1. The necessary calculations required a trial and error procedure of considerable complexity. When these calculations are performed correctly, however, the data will converge rapidly on the solution.

The calculations were begun for the first reactor by making assumptions concerning the fraction of unreacted methane per pass and the fraction of methane in the purge stream. These assumptions were best guesses. Using these assumptions material balances were performed and the process was repeated with new approximations.

The recycle ratios were specified independently of the other variables. This approach was realistic since in actual practice a plant can vary the recycle stream simply by adjusting the compressor setting. In this example the recycle ratio was set at 6.0 for both reactors. This is close to the inflection point: higher values result in significantly increased operating costs while lower values lead to much larger formation of byproducts.

The results for this example indicate that for a natural gas stream containing 7 percent inerts on a volume basis, 7.5 percent of the methane in the feed will be lost in the purge.

EXAMPLE 2

A third reactor was added to the arrangement which was described in Example 1. With this new layout the vent from the second reactor was fed to the third reactor, which was purged to the atmosphere. The recycle ratio for each of the reactors was set at 6.0. Again the natural gas source contained 7 percent inerts by volume. In this case 2.6 percent of the methane in the gas feed was vented. Thus, the addition of a third reactor greatly improved the methane efficiency.

EXAMPLE 3

In order to compare the use of multiple reactors with the use of a single reactor, calculations were done for a single reactor, a recycle ratio of 6.0, and inerts in the natural gas feed of 7 percent. These conditions led to a methane loss of 21.6 percent.

The results from Examples 1, 2, and 3 show a dramatic effect of the number of reactors on the loss of methane in the purge stream. Thus, by increasing the number of reactors the methanol yield can be increased significantly. On the other hand, the change in the number of reactors had little effect on the formation of byproducts. This fact was due to the condition that the recycle ratio was held constant at 6.0 for all cases. Under these circumstances the excess of natural gas in the feed to each reactor did not vary.

The results from Examples 1, 2, and 3 are summarized in the following table:

| Example | Number of Reactors | Vented Methane Loss | Volume Basis Inerts | Recycle Ratio |
|---------|-------------------|---------------------|---------------------|---------------|
| 1 | 2 | 7.5% | 7% | 6.0 |
| 2 | 3 | 2.6% | 7% | 6.0 |
| 3 | 1 | 21.6% | 7% | 6.0 |

This table shows that all parameters except the number of reactors were kept constant. Thus, the settings for the recycle ratio in all these examples were the same, namely, 6.0. Since the recycle ratio determines the amounts of excess methane used, the formation of undesired side reactions was constant irrespective of the number of reactors. This effect was previously disclosed in the aforementioned reference U.S. Pat. No. 5,185,479: "the formation of these higher chlorinated compounds is suppressed by using an excess of methane." (Column 4, lines 1–3)

In the above examples the only parameter which was changed was the number of reactors. The results were no less than dramatic. Simply by adding a second reactor the loss of methane in the purge stream was reduced from 21.6% for one reactor to 7.5% for two reactors. The addition of a third reactor decreased the methane losses even further resulting in a value of 2.6%. Although calculations were not made for 4 or more reactors, an extrapolation of the data suggests that methane losses can be reduced even further.

In conclusion, the data which are presented in the above table indicate that by employing multiple reactors the loss of methane can be controlled even though there is no appreciable effect on the formation of byproducts. These results point to a unique and unexpected benefit of using a cross-flow reactor system for the production of methanol from natural gas.

The embodiments of the present invention in which exclusive property or privilege is claimed are defined as follows:

1. A process for the production of methyl alcohol from natural gas which gas contains inerts in excess of 0.1 percent by volume, comprising the following steps:

reacting methyl chloride, hydrogen chloride, oxygen and perchloroethylene in a catalytic reactor to give reaction products comprising methyl alcohol and hexachloroethane, separating the methyl alcohol from the hexachloroethane, reacting the isolated hexachloroethane with said natural gas in multiple thermal chlorination reactors comprising at least first and second thermal chlorination reactors, to produce methyl chloride, hydrogen chloride, perchloroethylene and unreacted natural gas, said reactors being arranged in a cross-flow reactor system such that the natural gas is fed to the first reactor, and further such that a purge stream from said first reactor is fed to the second reactor, and so on until the last reactor, which is vented to the atmosphere by feeding a purge stream from said last reactor to the catalytic reactor, separating methyl chloride, hydrogen chloride and perchloroethylene from unreacted natural gas in the exit streams from each of the respective thermal chlorination reactors, recycling the resulting natural gas streams back to the respective thermal reactors, and returning the separated methyl chloride, hydrogen chloride and perchloroethylene to the catalytic reactor.

2. A process according to claim 1 in which methyl chloride, hydrogen chloride, and perchloroethylene are separated from unreacted natural gas in each exit gas stream by first cooling the gas stream to condense perchloroethylene and methyl chloride and then scrubbing said gas in an absorber with methyl alcohol to remove hydrogen chloride and any additional methyl chloride.

3. A process according to claim 2 in which the spent methyl alcohol containing hydrogen chloride and any methyl chloride is fed to the catalytic reactor.

4. A process according to claim 2 in which a second absorber is used to remove methyl alcohol vapors from the hydrogen chloride-free gas stream by scrubbing this gas stream with the condensate from the exit gas stream.

5. A process according to claim 4 in which the spent condensate is fed to the catalytic reactor.

* * * * *